US012767926B2

(12) United States Patent
Zhou et al.

(10) Patent No.: US 12,767,926 B2
(45) Date of Patent: Oct. 20, 2026

(54) ENGINEERED MITOCHONDRIA AND PREPARATION METHOD THEREOF

(71) Applicant: CHONGQING UNIVERSITY OF TECHNOLOGY, Chongqing (CN)

(72) Inventors: Xing Zhou, Neijiang (CN); Xuemei Li, Chongqing (CN); Hanyi Zhang, Chongqing (CN); Qing Zhang, Chongqing (CN)

(73) Assignee: CHONGQING UNIVERSITY OF TECHNOLOGY, Chongqing (CN)

( * ) Notice: Subject to any disclaimer, the term of this patent is extended or adjusted under 35 U.S.C. 154(b) by 391 days.

(21) Appl. No.: 18/490,773

(22) Filed: Oct. 20, 2023

(65) Prior Publication Data

US 2024/0043792 A1 Feb. 8, 2024

Related U.S. Application Data

(63) Continuation of application No. PCT/CN2022/087837, filed on Apr. 20, 2022.

(30) Foreign Application Priority Data

Apr. 26, 2021 (CN) ........................ 202110454259.3

(51) Int. Cl.
*C12N 5/00* (2006.01)
*C12N 1/066* (2026.01)
*C12N 5/0793* (2010.01)

(52) U.S. Cl.
CPC ........... *C12N 5/0006* (2013.01); *C12N 1/066* (2013.01); *C12N 5/0619* (2013.01)

(58) Field of Classification Search
None
See application file for complete search history.

(56) References Cited

FOREIGN PATENT DOCUMENTS

| | | | |
|---|---|---|---|
| CN | 105255835 | | 1/2016 |
| CN | 107446884 | A | 12/2017 |
| CN | 110022884 | A | 7/2019 |
| CN | 110627875 | A | 12/2019 |
| CN | 110790783 | A | 2/2020 |
| CN | 112020553 | A | 12/2020 |
| WO | 2017060418 | A1 | 4/2017 |
| WO | 2021004477 | A1 | 1/2021 |

OTHER PUBLICATIONS

Oh et al. "Reduced mitophagy in the cochlea of aged C57BI/6J mice" (2020) Experiment Gerontology, vol. 137, No. 110946: 1-9. (Year: 2020).*
Mccully et al. "Mitochondrial transplantation for therapeutic use" (2016), Clin Trans Med, S:16, 1-13. (Year: 2016).*
International Search Report issued in corresponding International application No. PCT/CN2022/087837, mailed Jul. 20, 2022.
Written Opinion of the International Search Authority in corresponding International application No. PCT/CN2022/087837, mailed Jul. 20, 2022.

* cited by examiner

*Primary Examiner* — Teresa E Knight

(57) ABSTRACT

The invention provides engineered mitochondria and a preparation method thereof, and relates to the technical field of mitochondria. The engineered mitochondria are formed by attaching exogenous cell membranes to outer membranes of exogenous mitochondria. The preparation method comprises the following steps: S1: extracting exogenous cell membranes from cells; S2: separating and extracting exogenous mitochondria from cells or tissue; and S3: mixing the separated and extracted exogenous mitochondria with the exogenous cell membranes in a specific ratio, thereby attaching the exogenous cell membranes to the outer membranes of the exogenous mitochondria to obtain the engineered mitochondria. The invention enables the production of engineered mitochondria with enhanced biological activity, exhibiting improved therapeutic effects on mitochondrial dysfunction-related disorders.

12 Claims, 8 Drawing Sheets

ENGINEERED MITOCHONDRIA AND PREPARATION METHOD THEREOF

BACKGROUND OF THE INVENTION

1. Technical Field

The invention relates to the technical field of mitochondria, in particular to engineering mitochondria and a preparation method thereof.

2. Description of Related Art

Mitochondria are organelles that provide energy in cells, supplying 90% of ATP in human cells and regulating cell apoptosis. Mitochondrial dysfunction will cause ATP synthesis disorder, leading to inadequate energy supply to the cells and giving rise to a range of diseases.

Currently, biologically active free mitochondria can be separated and extracted from cells or tissue, which can be administered intravenously or locally, enabling targeted delivery of exogenous mitochondria to an affected site to replace damaged mitochondria, and these exogenous mitochondria are able to restore normal mitochondrial function within the body, so as to effectively treat mitochondrial dysfunction-related diseases.

However, biologically active free mitochondria separated and extracted from cells or tissue are extremely unstable, and will soon lose their normal biological activity. Moreover, they lack targeted effects on affected tissue, which results in unsatisfactory therapeutic outcomes for mitochondrial dysfunction-related diseases.

BRIEF SUMMARY OF THE INVENTION

The first object of the invention is to provide a preparation method of engineered mitochondria. The invention enables the production of engineered mitochondria with enhanced biological activity, exhibiting improved therapeutic effects on mitochondrial dysfunction-related disorders.

The second object of the invention is to provide engineered mitochondria, which are prepared by the preparation method and have high biological activity and good therapeutic effects on mitochondrial dysfunction-related disorders.

The embodiment of the invention is realized by the following technical scheme:

Engineered mitochondria are formed by attaching exogenous cell membranes to outer membranes of exogenous mitochondria.

Normal mitochondria exist in the matrix of cells and are adapted to a membranous environment. In this invention, exogenous cell membranes are attached to outer membranes of exogenous mitochondria, providing a membrane-like environment for exposed exogenous mitochondria and thereby stabilizing the biological activity of the exogenous mitochondria.

Further, the exogenous cell membrane is extracted and prepared from any one of neutrophils, monocytes, lymphocytes or tumor cells.

Further, the exogenous mitochondria are separated from cells or tissue.

Further, the tissue is selected from any one of myocardial tissue, liver tissue, brain tissue, muscle tissue, blood or interstitial fluid.

A preparation method of the engineered mitochondria comprises the following steps:

S1: extracting exogenous cell membranes (NEM) from cells;

S2: separating and extracting exogenous mitochondria (Mito) from cells or tissue; and S3: mixing the separated and extracted exogenous mitochondria with the exogenous cell membranes in a specific ratio, thereby attaching the exogenous cell membranes to the outer membranes of the exogenous mitochondria to obtain the engineered mitochondria (NEM-Mito).

Further, in S1, cells are extracted from tissue using a kit, then the cells are broken by a mechanical method, and the exogenous cell membranes are obtained after freeze-drying.

Further, in S2, cells or tissue is used to separate and extract the exogenous mitochondria through a cell mitochondrial isolation kit.

Further, in S3, the exogenous mitochondria and the exogenous cell membranes are mixed according to a protein mass ratio of 1:1-1:4.

The exogenous cell membranes are effectively attached to the outer membranes of the exogenous mitochondria, creating a membrane-like environment outside the exogenous mitochondria to enhance biological activity.

Further, in S3, the exogenous mitochondria and the exogenous cell membranes are mixed in a specific ratio in an appropriate amount of 0.01 M PBS solution; the mixture is subjected to 2-5 minutes of ultrasonication in a water bath at 4° C., followed by centrifugation at 3500 g for 10-15 minutes; a supernatant is discarded, and washing and precipitation are conducted 2-3 times with the 0.01 M PBS solution to remove unattached exogenous cell membranes; finally, centrifugation is conducted at 3500 g for 10-15 minutes at 4° C. to obtain the engineered mitochondria.

Further, C57BL/6J mice are used to extract the exogenous cell membranes and the exogenous mitochondria in S1 and S2.

The technical scheme of the embodiment of the invention has at least the following advantages and beneficial effects:

According to the invention, the engineered mitochondria are prepared by attaching the exogenous cell membranes to the outer membranes of the biologically active exogenous mitochondria which are obtained by separation and extraction, so that the engineered mitochondria have higher biological activity than naked exogenous mitochondria, and the therapeutic effects on mitochondrial dysfunction-related disorders are better.

DETAILED DESCRIPTION OF THE INVENTION

Figure 1:
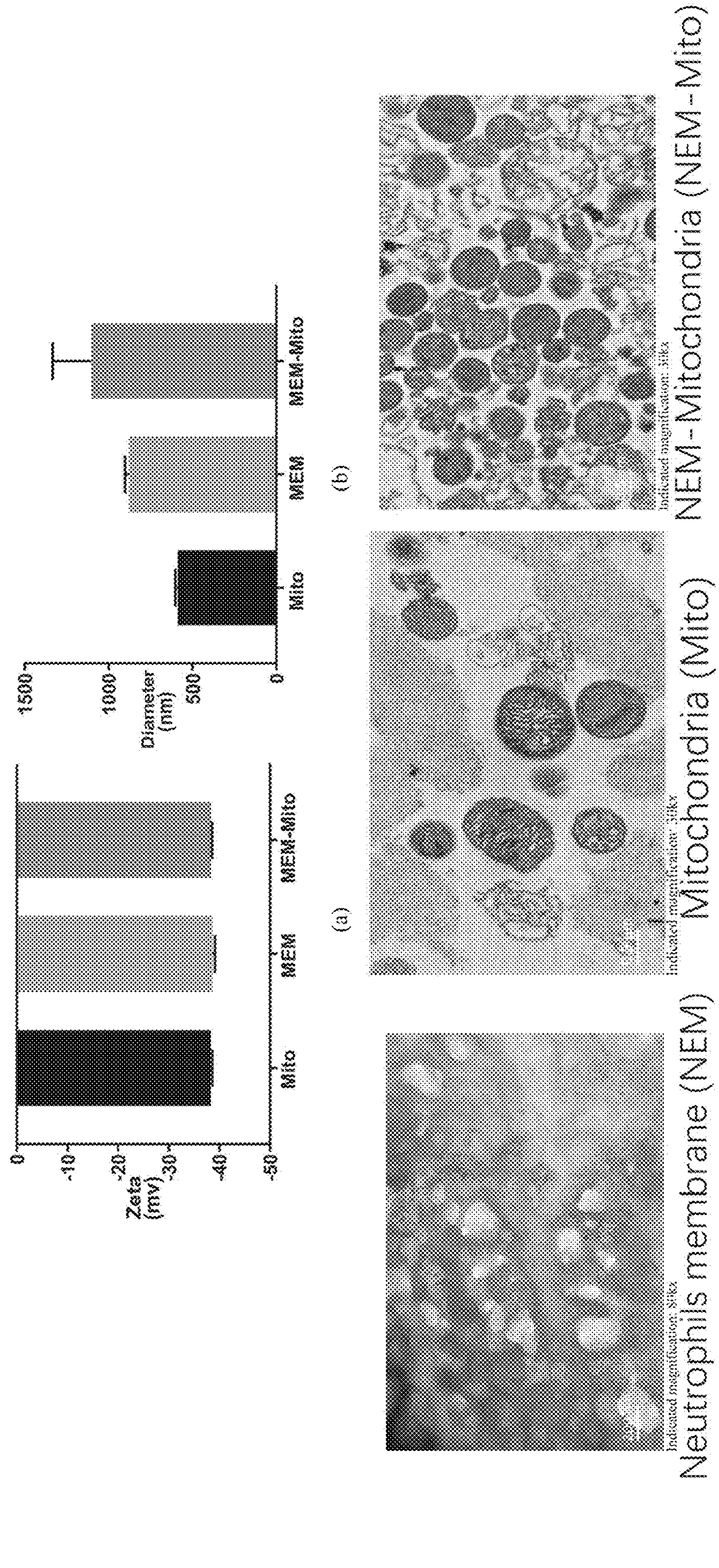
FIG. 1 is a result diagram provided by Experimental example 1, where Chart (a) illustrates zete potential, Chart (b) illustrates particle size, and Chart (c) illustrates a transmission electron microscopy (TEM) image.

In order to make the purpose, technical scheme and advantages of the embodiments of the invention more clear, the technical scheme in the embodiments of the invention will be described clearly and completely below. If no specific conditions are indicated in the embodiments, conventional conditions or the conditions suggested by the manufacturer are adopted. Reagents or instruments not marked with manufacturers are conventional products that are available in the market.

Engineered mitochondria and a preparation method thereof provided by the embodiments of the invention will be described in detail below.

Embodiment 1

This embodiment provides engineered mitochondria which are formed by attaching exogenous cell membranes to outer membranes of exogenous mitochondria.

This embodiment provides a preparation method of the engineered mitochondria, which comprises the following steps:

S1: neutrophils were separated and extracted from C57BL/6J mouse bone marrow using a Solarbio mouse bone marrow neutrophil isolation kit, the neutrophils were then disrupted through probe ultrasonication, and exogenous neutrophil membrane fragments were obtained after freeze-drying;

S2: exogenous mitochondria were separated and extracted from C57BL/6J mouse myocardial tissue using a Beyotime cell mitochondria isolation kit; and S3: the exogenous mitochondria and the exogenous neutrophil membrane fragments were mixed in an appropriate amount of 0.01 M PBS solution in a protein mass ratio of 1:1, and the mixture was subjected to 2 minutes of ultrasonication in a water bath at 4° C., followed by centrifugation at 3500 g for 10 minutes; a supernatant was discarded, and washing and precipitation were conducted 2 times with the 0.01 M PBS solution to remove unattached exogenous neutrophil membrane fragments; finally, centrifugation was conducted at 3500 g for 10 minutes at 4° C. to obtain the engineered mitochondria.

Embodiment 2

This embodiment provides engineered mitochondria which are formed by attaching exogenous cell membranes to outer membranes of exogenous mitochondria.

This embodiment provides a preparation method of the engineered mitochondria, which comprises the following steps:

S1: monocytes were separated and extracted from C57BL/6J mouse liver tissue using a Solarbio mouse organ tissue monocyte isolation medium kit, the monocytes were then disrupted through oscillation, and exogenous monocyte membrane fragments were obtained after freeze-drying;

S2: exogenous mitochondria were separated and extracted from C57BL/6J mouse liver tissue using a Solarbio mitochondria isolation kit; and S3: the exogenous mitochondria and the exogenous monocyte membrane fragments were mixed in an appropriate amount of 0.01 M PBS solution in a protein mass ratio of 1:2, and the mixture was subjected to 4 minutes of ultrasonication in a water bath at 4° C., followed by centrifugation at 3500 g for 15 minutes; a supernatant was discarded, and washing and precipitation were conducted 3 times with the 0.01 M PBS solution to remove unattached exogenous monocyte membrane fragments; finally, centrifugation was conducted at 3500 g for 15 minutes at 4° C. to obtain the engineered mitochondria.

Embodiment 3

This embodiment provides engineered mitochondria which are formed by attaching exogenous cell membranes to outer membranes of exogenous mitochondria.

This embodiment provides a preparation method of the engineered mitochondria, which comprises the following steps:

S1: lymphocytes were separated and extracted from C57BL/6J mouse spleen tissue using a Solarbio mouse splenic lymphocyte isolation medium kit, the lymphocytes were then disrupted through probe ultrasonication, and exogenous lymphocyte membrane fragments were obtained after freeze-drying;

S2: exogenous mitochondria were separated and extracted from C57BL/6J mouse brain tissue using a Solarbio mitochondria isolation kit; and S3: the exogenous mitochondria and the exogenous lymphocyte membrane fragments were mixed in an appropriate amount of 0.01 M PBS solution in a protein mass ratio of 1:4, and the mixture was subjected to 5 minutes of ultrasonication in a water bath at 4° C., followed by centrifugation at 3500 g for 15 minutes; a supernatant was discarded, and washing and precipitation were conducted 3 times with the 0.01 M PBS solution to remove unattached exogenous lymphocyte membrane fragments; finally, centrifugation was conducted at 3500 g for 15 minutes at 4° C. to obtain the engineered mitochondria.

Experimental Example 1

The Zeta potential and particle size of the free neutrophil membrane fragments (NEM), the exogenous mitochondria (Mito) and the engineered mitochondria (NEM-Mito) obtained in Embodiment 1 were measured, and were imaged using TEM, as shown in FIG. 1.

As can be seen from FIG. 1, the particle size of the NEM-Mito prepared in Embodiment 1 of the invention is 1104.55±227.97 nm, and the Zeta potential is −38±0.26 mV.

Experimental Example 2

The ATP level of the engineered mitochondria (NEM-Mito) and the exogenous mitochondria (Mito) obtained in Embodiment 1 were tested using a Beyotime enhanced ATP assay kit, and the mitochondrial membrane potential (MMP) was tested using a Beyotime mitochondrial membrane potential detection kit (JC-1). The results are shown in FIG. 2.

Figure 2:
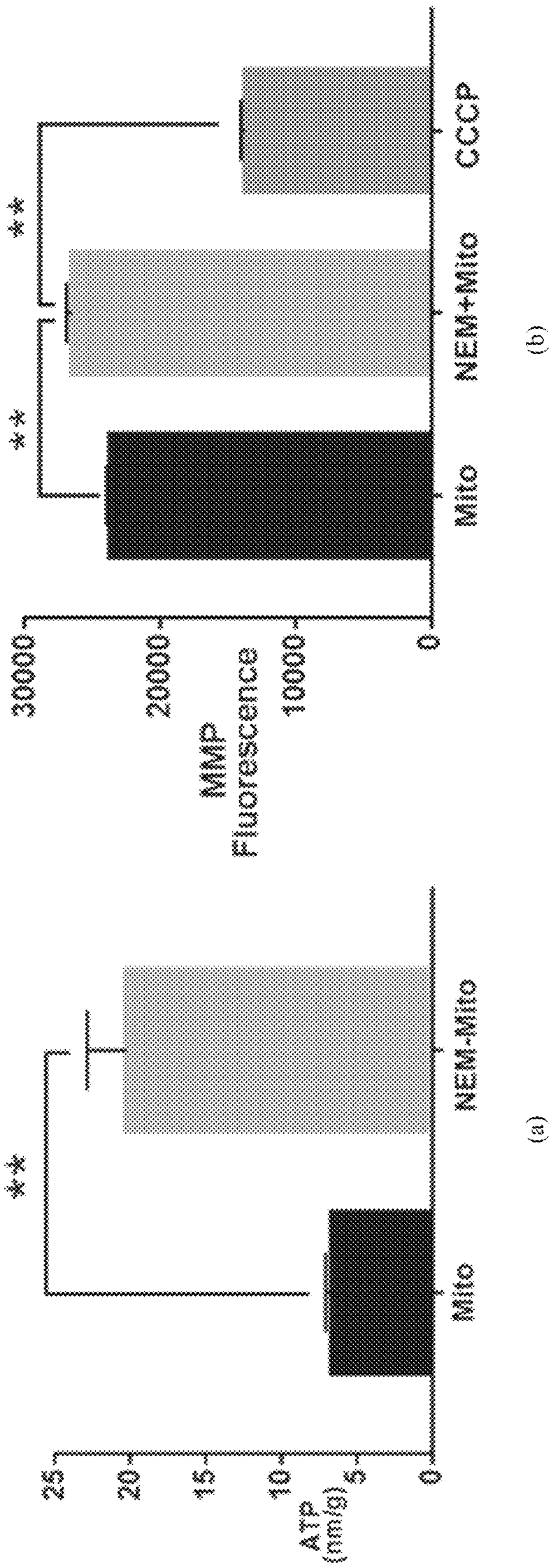
FIG. 2 is a result diagram provided by Experimental example 2, where Chart (a) illustrates ATP level, and Chart (b) illustrates mitochondrial membrane potential (MMP) level.

As can be seen from FIG. 2, the ATP and MMP levels of the NEM-Mito prepared by the invention are significantly higher than those of Mito obtained by separation and extraction, indicating that the NEM-Mito prepared by the invention has better biological activity than Mito.

Experimental Example 3

1. Establish L02 Cell Model with Mitochondrial Dysfunction (1) Experimental L02 cells: A 1640 culture solution containing 10% serum was used for culture in a culture bottle, and subculture was conducted in a 37° C. sterile constant-temperature incubator containing 5% $CO_2$.

(2) Preparation of paracetamol (APAP) solution: APAP powder was fully dissolved in a 1640 culture solution containing 0.125% DMSO and 1% serum, and then prepared into an APAP solution with a certain concentration.

(3) Establishment of L02 cell model with mitochondrial dysfunction: After digesting an L02 cell suspension in the logarithmic phase, a six-well plate was used for inoculation, 2 ml in each well, the density of L02 cells was adjusted to $5\times10^3$ cells/well, culture was conducted in a 37° C. sterile constant-temperature incubator containing 5% $CO_2$ for 24 h until the well bottom of the six-well plate was covered with a cell monolayer, and then the upper layer of culture solution was sucked out; and the APAP solution was added to the wells, making the final concentration of APAP in the culture solution 10 mM, and culture was conducted in a 37° C. sterile constant-temperature incubator containing 5% $CO_2$ for 24 h, inducing the mitochondrial dysfunction of the L02 cells, increasing the release of ALT, AST and ROS, and decreasing the ATP and MMP levels.

2. Cell Experiment In Vitro 2 ml of exogenous mitochondria (Mito) and 2 ml of engineered mitochondria (NEM-Mito) obtained in Embodiment 1 with concentration gradients of 6.25 μg/ml, 12.5 μg/ml and 25 μg/ml were added to the L02 cell model with mitochondrial dysfunction in each well of a six-well plate, and three replicate wells were set for each concentration gradient; a blank group was set as 2 ml of 1640 culture solution containing 1% serum being added to normal L02 cells in each well of a six-well plate; and both groups were incubated in a 37° C. sterile constant-temperature incubator containing 5% CO 2 for 24 h.

Figure 3:
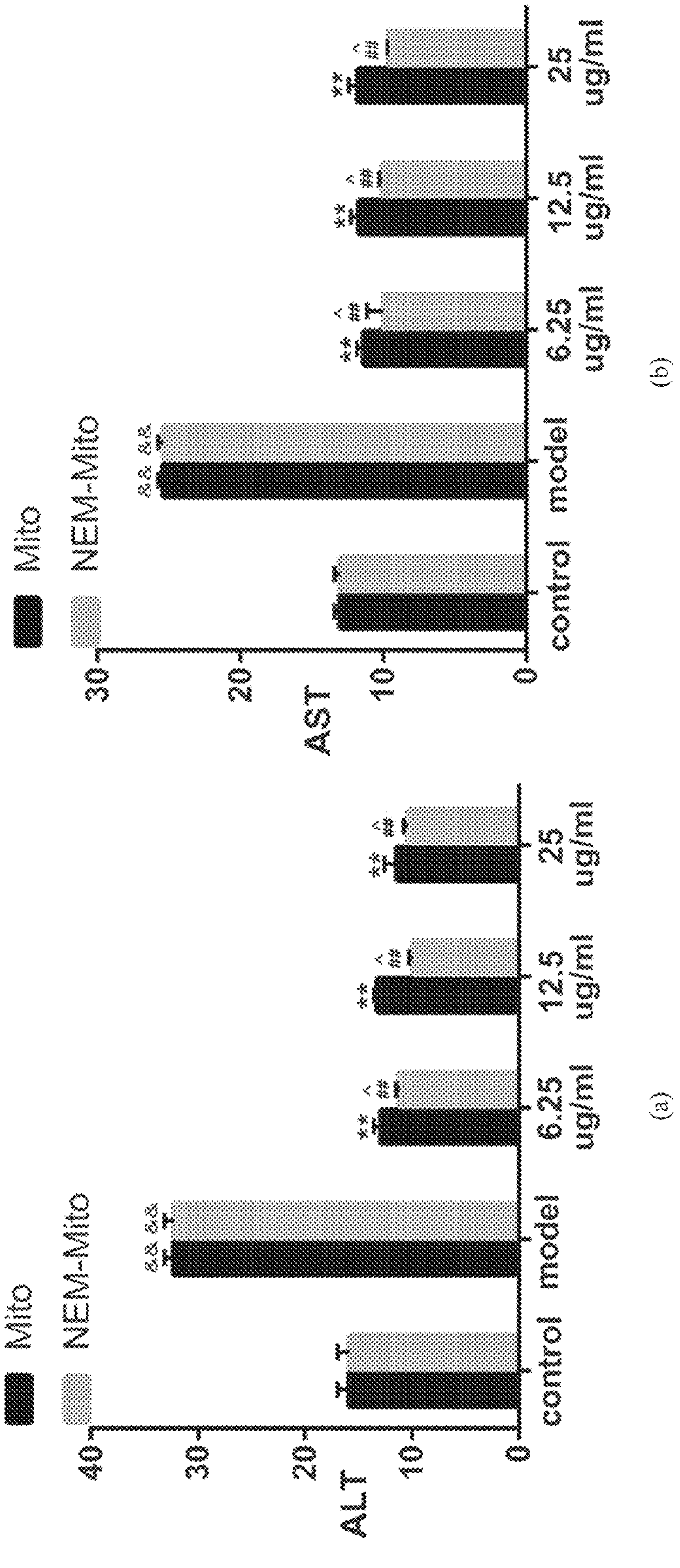
FIG. 3 is a result diagram provided by Experimental example 3, where Chart (a) illustrates ALT level, and Chart (b) illustrates AST level.
Figure 4:
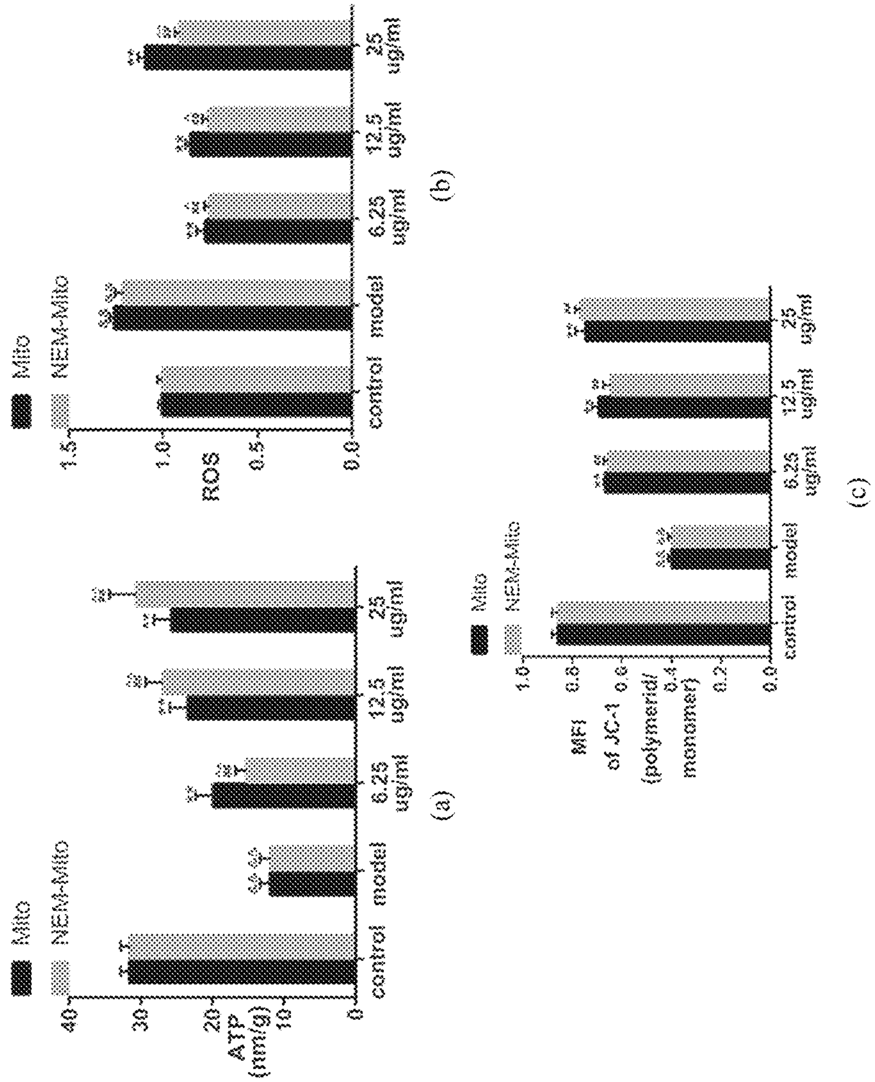
FIG. 4 is a result diagram provided by Experimental example 3, where Chart (a) illustrates ATP level, Chart (b) illustrates ROS level, and Chart (c) illustrates MMP level.

After incubation for 24 h, the levels of alanine transaminase (ALT) and aspartate transaminase (AST) in a cell supernatant were tested using a biochemical analyzer, and the results are shown in FIG. 3; and after incubation for 24 h, the levels of ATP, MMP and reactive oxygen species (ROS) in cell mitochondria were tested, the testing methods of ATP and MMP were the same as those in Experimental example 2, the level of ROS was tested using a DCFH-DA probe, and the results are shown in FIG. 4.

It can be seen from FIG. 3 that both the Mito obtained by separation and extraction and the NEM-Mito prepared by the invention can inhibit the release of ALT and AST in the L02 cell model with mitochondrial dysfunction; however, the NEM-Mito prepared by the invention exhibits stronger inhibition ability on the release of ALT and AST compared to the exogenous Mito obtained by separation and extraction.

It can be seen from FIG. 4 that both the exogenous Mito obtained by separation and extraction and the NEM-Mito prepared by the invention can inhibit the release of ROS in the L02 cell model with mitochondrial dysfunction, increasing the levels of ATP and MMP; however, the NEM-Mito prepared by the invention exhibits stronger inhibition ability on the release of ROS compared to the exogenous Mito obtained by separation and extraction, resulting in higher increases in ATP and MMP levels.

Experimental Example 4

1. Establish Mouse Model with Mitochondrial Dysfunction in Liver Cells (1) Experimental mice: Kunming mice, random allocation of males and females, 4-5 weeks old, weighing 18-22 g, leisurely grazing.

(2) Preparation of paracetamol (APAP) solution: APAP powder was thoroughly mixed with physiological saline, and then an equal volume of PEG400 was added to make a 400 mg/kg APAP solution.

(3) Establishment of a mouse model with mitochondrial dysfunction in liver cells: The mice were intraperitoneally injected with a one-time dose of 400 mg/kg APAP solution, at a dosage of 10 ml/kg; and the modeling time was 24 h, which induced elevated AST and ALT levels in mouse serum, mitochondrial dysfunction in liver cells, and hepatocyte rupture and apoptosis.

2. In Vivo Experiment with Mice

The exogenous Mito and NEM-Mito obtained in Embodiment 1 were prepared in physiological saline and PEG400 in a volume ratio of 1:1 to a concentration of 100 μg/mL; this solution was administered through tail vein injection to mice models with mitochondrial dysfunction in liver cells, at a dose of 10 mL/kg; a blank group was set as healthy Kunming mice receiving a mixture of physiological saline and PEG400 in a volume ratio of 1:1 through intravenous injection, also at a dose of 10 mL/kg; and each group consisted of 7 parallel sets.

Figure 5:
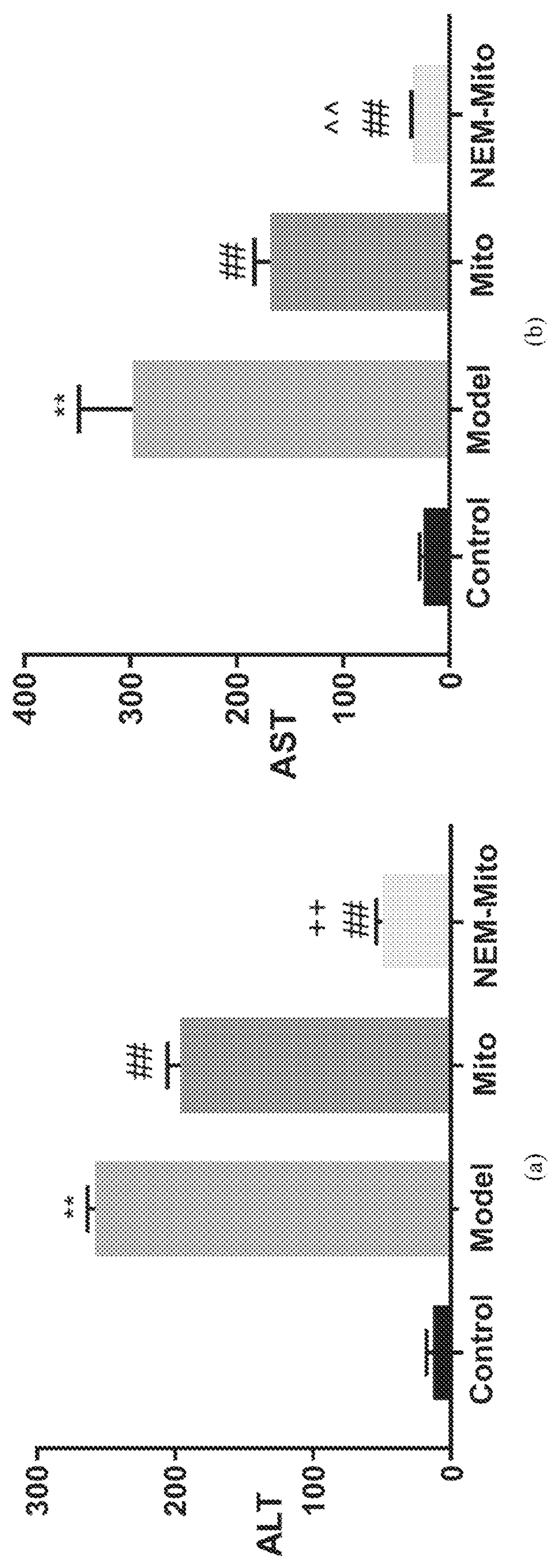
FIG. 5 is a result diagram provided by Experimental example 4, where Chart (a) illustrates ALT level, and Chart (b) illustrates AST level.
Figure 6:
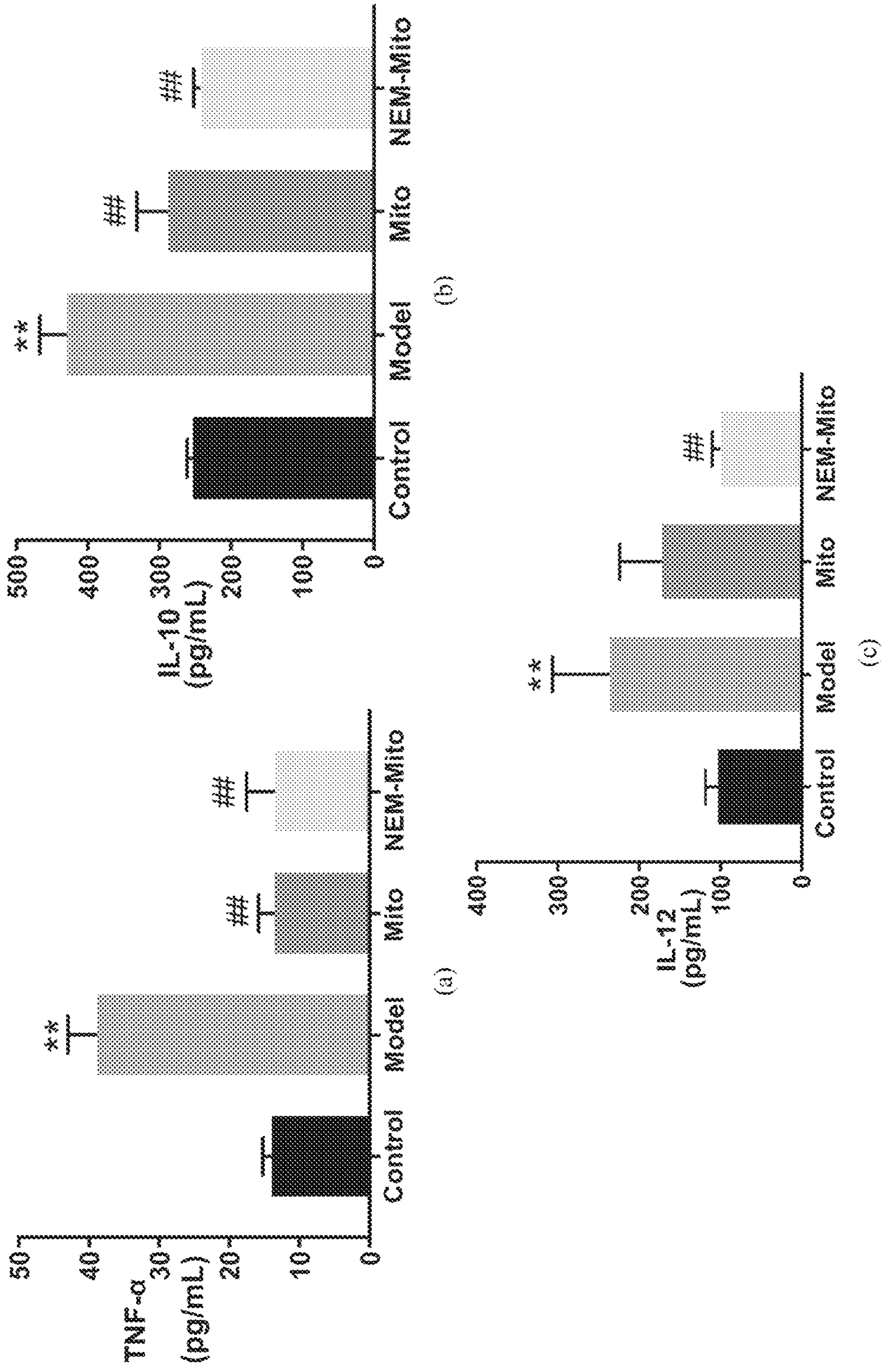
FIG. 6 is a result diagram provided by Experimental example 4, where Chart (a) illustrates IL-10 level, Chart (b) illustrates IL-12 level, and Chart (c) illustrates TNF-α level.
Figure 7:
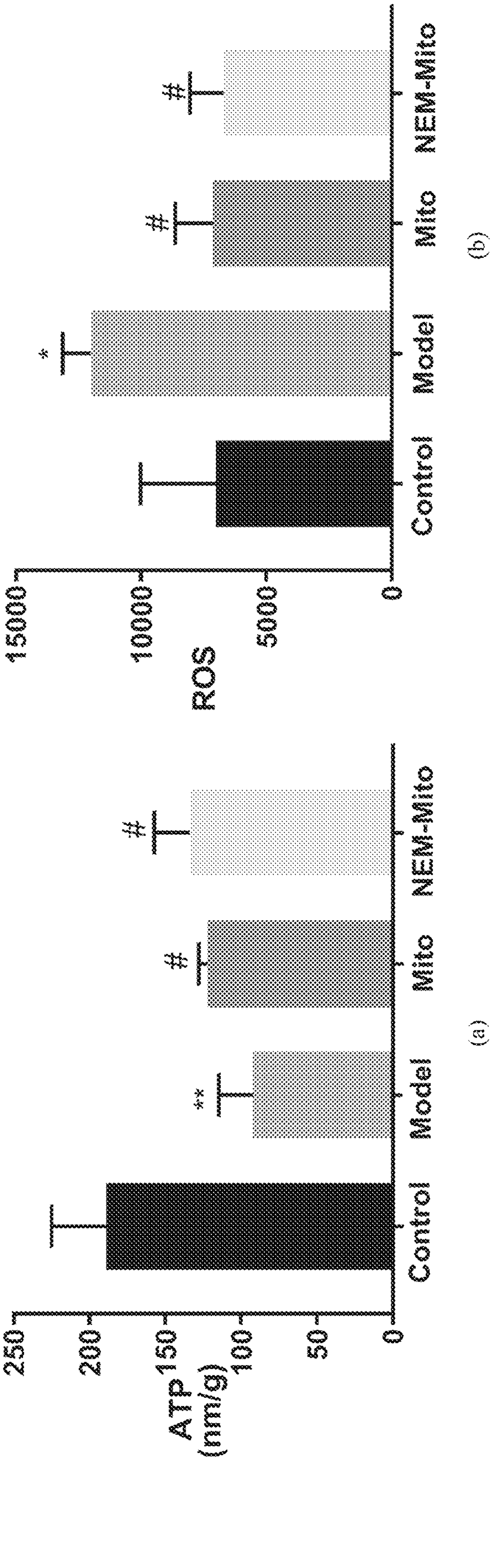
FIG. 7 is a result diagram provided by Experimental example 4, where Chart (a) illustrates ATP level, and Chart (b) illustrates ROS level.

The mice were killed 24 h after administration, the levels of AST and ALT in the serum were measured using a biochemical analyzer, and the results are shown in FIG. 5; the levels of inflammatory factors TNF-α, IL-10, and IL-12 in the serum were also measured, TNF-α was measured using a mouse TNF-α ELISA kit from Neobioscience, IL-10 was measured using a mouse IL-10 ELISA kit from Hangzhou MultiSciences Biotech, IL-12 was measured using a mouse IL-12 ELISA kit from Hangzhou MultiSciences Biotech, and the results are shown in FIG. 6; furthermore, the ATP and ROS levels in mitochondria in liver tissue of the mice were measured, the methods for testing ATP and ROS levels were the same as those in Experimental example 2, and the results are shown in FIG. 7.

Figure 8:
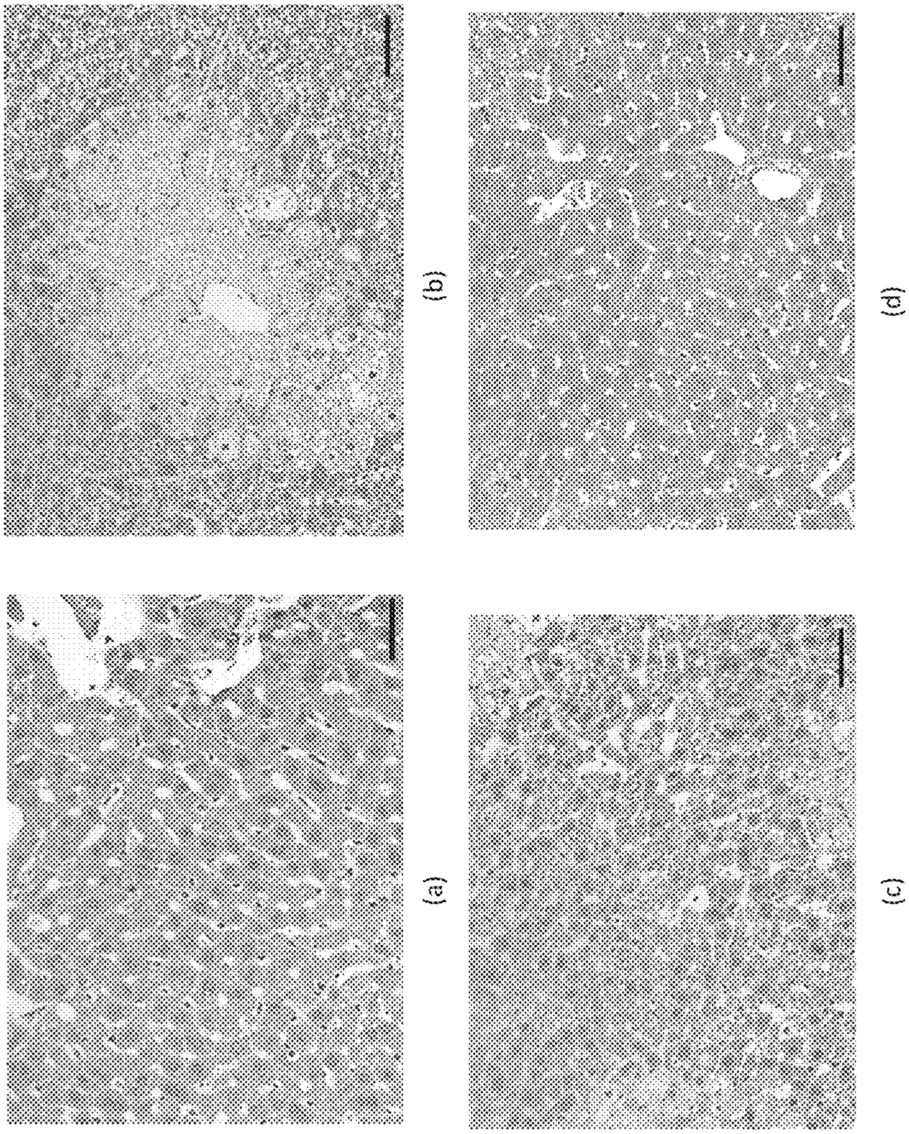
FIG. 8 is a result diagram provided by Experimental example 4, where Chart (a) illustrates the liver tissue of blank mice, Chart (b) illustrates the liver tissue of model mice, Chart (c) illustrates the liver tissue of Mito control mice, and Chart (d) illustrates the liver tissue of NEM-Mito experimental mice.

A separate group of experimental mice were used to prepare pathological sections from liver tissue. The results are shown in FIG. 8.

It can be seen from FIG. 5 that after treatment with the NEM-Mito prepared by the invention, the levels of AST and ALT in the serum of mice with mitochondrial dysfunction in liver cells were significantly reduced; and compared with the group of mice with mitochondrial dysfunction in liver cells treated with the exogenous Mito obtained from separation and extraction, the reduction in AST and ALT levels was more significant.

It can be seen from FIG. 6 that after treatment with the NEM-Mito prepared by the invention, the levels of inflammatory factors TNF-α, IL-10, and IL-12 in the serum of mice with mitochondrial dysfunction in liver cells were significantly reduced, inhibiting the aggregation of inflammatory factors in the mouse serum; and compared with the group of mice with mitochondrial dysfunction in liver cells treated with the exogenous Mito obtained from separation and extraction, the inhibitory effect was more significant.

It can be seen from FIG. 7 that after treatment with the NEM-Mito prepared by the invention, the ATP level in mitochondria in liver tissue of the mice with mitochondrial dysfunction in liver cells were significantly increased, and the release of ROS from mitochondria in liver tissue of the mice was significantly inhibited; and compared with the group of mice with mitochondrial dysfunction in liver cells treated with the exogenous Mito obtained from separation and extraction, the therapeutic effects were more significant.

It can be seen from FIG. 8 that after treatment with the NEM-Mito prepared by the invention, the damaged liver tissue of the mice with mitochondrial dysfunction in liver cells was repaired to a greater extent; and compared with the group of mice with mitochondrial dysfunction in liver cells treated with the exogenous Mito obtained from separation and extraction, the structure of hepatic lobules after treatment was more intact, the hepatocyte structure was restored to normal, and most of the nuclear structures were intact.

In summary, the engineered mitochondria (NEM-Mito) produced by this application have high biological activity and have good therapeutic effects on mitochondrial dysfunction.

The above embodiments are only preferred ones of the invention, and are not used to limit the invention. For those skilled in the art, the invention may have various modifications and changes. Any modification, equivalent substitution, improvement, etc. made within the spirit and principle of the invention should be included in the protection scope of the invention.

What is claimed is:

1. Engineered mitochondria formed by attaching exogenous cell membranes to outer membranes of exogenous mitochondria, a preparation method of the engineered mitochondria comprising the following steps:

S1: extracting exogenous cell membranes from cells;

S2: separating and extracting exogenous mitochondria from cells or tissue; and

S3: mixing the separated and extracted exogenous mitochondria with the exogenous cell membranes in a specific ratio, thereby attaching the exogenous cell membranes to the outer membranes of the exogenous mitochondria to obtain the engineered mitochondria; and wherein the exogenous cell membrane is derived from a first cell or tissue, and the exogenous mitochondria is derived from a second cell or tissue that is different from said first cell or tissue, wherein the exogenous cell membrane is only attached to a surface of the outer membrane of the exogenous mitochondria and does not form a vesicle structure encapsulating the exogenous mitochondria, and wherein the engineered mitochondria does not comprise lysosomes, autophagosomes or cytoplasmic impurities.

2. The engineered mitochondria according to claim 1, wherein the exogenous cell membranes are extracted and prepared from any one of neutrophils, monocytes, lymphocytes or tumor cells.

3. The engineered mitochondria according to claim 1, wherein the exogenous mitochondria are separated from cells or tissue.

4. The engineered mitochondria according to claim 3, wherein the tissue is selected from any one of myocardial tissue, liver tissue, brain tissue, muscle tissue, blood or interstitial fluid.

5. The engineered mitochondria according to claim 1, wherein in S1, cells are extracted from tissue, then the cells are broken by a mechanical method, and the exogenous cell membranes are obtained after freeze-drying.

6. The engineered mitochondria of claim 5, further comprising a quality control step of detecting endotoxin content to ensure it is less than 0.1 EU/mg of protein.

7. The engineered mitochondria according to claim 1, wherein in S2, cells or tissue is used to separate and extract the exogenous mitochondria through a cell mitochondrial isolation kit.

8. The engineered mitochondria according to claim 1, wherein in S3, the exogenous mitochondria and the exogenous cell membranes are mixed according to a protein mass ratio of 1:1-1:4.

9. The engineered mitochondria according to claim 1, wherein in S3, the exogenous mitochondria and the exogenous cell membranes are centrifuged, washed and precipitated after being mixed in a specific ratio, and unattached exogenous cell membranes are removed to obtain the engineered mitochondria.

10. The engineered mitochondria according to claim 1, wherein C57BL/6J mice are used to extract the exogenous cell membranes and the exogenous mitochondria in S1 and S2.

11. The engineered mitochondria of claim 1, wherein the exogenous cell membrane is non-covalently attached to the outer membrane of the exogenous mitochondria via electrostatic interactions and hydrophobic forces.

12. The engineered mitochondria of claim 1, wherein the exogenous cell membrane comprises surface markers that enhance targeting to cardiac muscle cells or neurons.

* * * * *